United States Patent [19]

Clausen et al.

[11] Patent Number: 4,854,935
[45] Date of Patent: Aug. 8, 1989

[54] 5-ALKOXY-2,4-DIAMINO-ALKYL-BENZENES AND HAIRDYE COMPOSITIONS BASED ON 5-ALKOXY-2,4-DIAMINO-ALKYL-BENZENES

[75] Inventors: Thomas Clausen, Alsbach; Eugen Konrad, Darmstadt, both of Fed. Rep. of Germany

[73] Assignee: Wella Aktiengesellschaft, Darmstadt, Fed. Rep. of Germany

[21] Appl. No.: 165,278

[22] PCT Filed: Jun. 20, 1987

[86] PCT No.: PCT/EP87/00320
§ 371 Date: Feb. 26, 1988
§ 102(e) Date: Feb. 26, 1988

[87] PCT Pub. No.: WO88/00042
PCT Pub. Date: Jan. 14, 1988

[30] Foreign Application Priority Data

Jul. 7, 1986 [DE] Fed. Rep. of Germany ....... 3622784

[51] Int. Cl.$^4$ .................... A61K 7/13; C07C 91/40; C07C 87/52
[52] U.S. Cl. ............................ 8/408; 8/411; 8/416; 8/421; 564/443; 564/305
[58] Field of Search ............... 8/408, 411, 416, 421; 564/443, 305

[56] References Cited

U.S. PATENT DOCUMENTS

| 4,031,160 | 6/1977 | Kalopissis et al. | 8/416 |
| 4,125,367 | 11/1978 | Bugaut et al. | 8/408 |
| 4,171,203 | 10/1979 | Rose et al. | 8/416 |
| 4,323,360 | 4/1982 | Bugaut et al. | 8/408 |
| 4,324,553 | 4/1982 | Bugaut et al. | 8/408 |
| 4,566,876 | 1/1986 | Brown et al. | 8/411 |

OTHER PUBLICATIONS

John F. Corbett, Benzoquinone Imines etc., J. Chem. Soc., Perkin Trans., 2, 1972, pp. 999–1005.

Primary Examiner—Prince E. Willis
Assistant Examiner—Helene Kirschner
Attorney, Agent, or Firm—Michael J. Striker

[57] ABSTRACT

New 5-alkoxy-2,4-diaminoalkylbenzenes is disclosed having the formula (I)

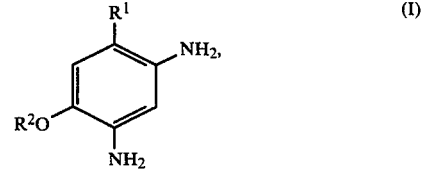

where $R^1$ is methyl or ethyl and $R^2$ is an alkyl radical having from 2 to 4 carbon atoms, a monohydroxyalkyl radical having from 2 to 4 carbon atoms or a dihydroxyalkyl radical having from 3 to 4 carbon atoms, as well as their acid addition salts, and oxidative hair dyeing compositions containing compounds of formula (I).

10 Claims, No Drawings

5-ALKOXY-2,4-DIAMINO-ALKYL-BENZENES AND HAIRDYE COMPOSITIONS BASED ON 5-ALKOXY-2,4-DIAMINO-ALKYL-BENZENES

The subject of the invention is new 5-alkoxy-2,4-diaminoalkylbenzenes and compositions for oxidative hair coloring based on known developer substances and 5-alkoxy-2,4-diaminoalkylbenzenes as coupler substances.

For hair coloring, oxidation dyes have attained substantial significance. Here the coloring is produced by the reaction of particular developer substances with particular coupler substances, in the presence of a suitable oxidation agent.

The coupler substances preferably used are m-phenylenediamine and its derivatives, such as 2,4-diaminoanisole, 2,4-diaminophenetole, 2,4-diaminophenoxyethanol, 3,5-diamino-2,6-dimethoxypyridine, 2-amino-4-(2'-hydroxyethyl)aminoanisole, as blue couplers; 1-naphthol, m-aminophenol, 3-amino-5-hydroxy-2,6-dimethoxypyridine, and 5-amino-o-cresol, as red couplers; and resorcin, 2-methylresorcin and 4-chlororesorcin, as couplers for the brown-blonde range.

Preferred developer substances are 2,5-diaminotoluol, 4-aminophenol and 1,4-diaminobenzene, but 2,5-diaminoanisole, 2,5-diaminobenzylalcohol and 2-(2'-hydroxyethyl)-1,4-diaminobenzene have also attained a certain importance. In particular cases, tetraaminopyrimidine can also be used as a developer substance.

Numerous special requirements are made for oxidation dyes used for coloring human hair. For instance, they must be toxicologically and dermatologically unobjectionable, and must enable the attainment of colorings having the desired intensity. It is also necessary to be able to produce a broad palette of different shades, by combining suitable developer and coupler substances. Furthermore, the attainable hair dyes must have good light fastness, permanent wave fastness, and acid resistance and must not rub off. In each case, however, such hair dyes must remain stable, without being affected by light, chemicals and rubbing, over a period of at least 4 to 6 weeks.

Although the combinations of the above-mentioned developer and coupler substances used at the present time in hair dye compositions do largely meet these requirements in terms of their technical application properties, they cannot satisfactorily meet the requirements in terms of toxicological properties. In particular, it is now being required that compounds used in hair dye compositions be non-mutagenic, or only slightly mutagenic, in test systems such as those of B. N. Ames.

For instance, 2,4-diaminotoluol, which has good coloring properties, is prohibited in many countries as a hair dye because of its mutagenic action.

A reddish tinge such as is obtained with the known coupler substance 2-amino-4-(2'-hydroxyethyl)aminoanisole, makes it difficult to attain a range of shades, because the proportion of red that is obtained in addition to the desired blue has to be compensated for by the addition of further color components. The shift of the depth of tone that then occurs must also be taken into consideration.

A green tinge, resulting for example from dyeing with 3,5-diamino-2,6-dimethoxypyridine, is also problematic. This kind of green tinge makes it difficult to produce ash-blonde tones, in which a bluish highlight is desirable. Compensating for the greenish coloring again necessitates the addition of further color components, which once again makes it more difficult to attach gradations of light tones.

2,4-Diamino-5-tetrafluoroethoxytoluol, known from the applicant's own German Patent Disclosure Document DE-OS No. 3 430 513, although it exhibits no mutagenic action in the Ames test, nevertheless is not completely satisfactory in terms of color depths and light fastness of the colors attainable with this compound. Furthermore, pure 2,4-diamino-5-tetrafluoroethoxytoluol can be produced only with expensive chromatographical separations on the gram scale, so that hair dye compositions containing 2,4-diamino-5-tetrafluoroethoxytoluol are much more expensive.

It is therefore the object of the invention to furnish a hair dye composition based on novel coupler substances which can be produced and inexpensively, and which in combination with suitable developer substances yield a pure blue coloration of great depth of color and light fastness and have physiologically favorable properties.

To this end, it has now been found, unexpectedly, that the toxicological properties of particular coupler substances typically used in oxidation hair dye compositions can be improved substantially by introducing various alkoxy groups into these compositions.

The subject of the invention is therefore new 5-alkoxy-2,4-diaminoalkylbenzenes having the formula (I)

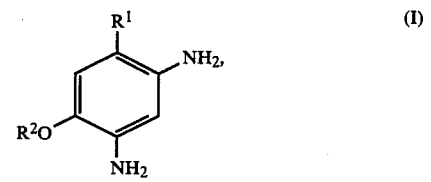

where $R^1$ is methyl or ethyl and $R^2$ is an alkyl radical having from 2 to 4 carbon atoms, a monohydroxyalkyl radical having from 2 to 4 carbon atoms or a dihydroxyalkyl radical having from 3 to 4 carbon atoms, as well as its acid addition salt.

As examples for the new coupler substances of formula (I), 2,4-diamino-5-(2'-hydroxyethyl)oxytoluol and 2,4-diamino-5-ethoxytoluol can be named.

The preparation of representative examples of the new coupler substances is described in the examples. The compounds can generally be prepared in two ways:

1. 5-Chloro-2,4-dinitrotoluol (M. Qvist and M. Moilanen, Acta Acad. Aboenis, Math. Phys., 14 (1943); C. A. 38, 5491 (1944)) is converted with the corresponding alcohol, in which potassium hydroxide has previously been dissolved, in accordance with the process given by J. F. Corbett, J. Chem. Soc. Perkin II, 999 (1972).

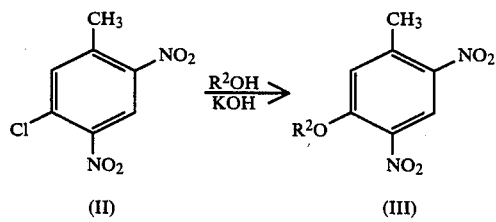

The catalytic reduction of (III) produces the coupler substance having the formula (I) where $R^1 = CH_3$.

2. 2,4-Dinitro-5-alkylphenol is alkylated at the hydroxy group. For example, the 2,4-dinitro-5-alkylphenol (IV) (J. R. Gibbs and P. W. Robertson, J. Chem. Soc. (London) 105, 1885–1892) by conversion with an optionally substituted alkyl halide, can be converted into the precursor (III), the catalytic reduction of which produces (I) as above.

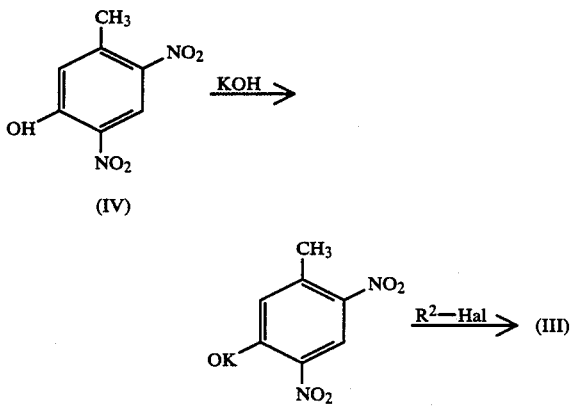

The preparation of the formula (I) compounds by alkylation of the phenol precursor or by nucleophilic substitution of the chlorobenzene precursor can be performed simply and hence inexpensively on an industrial scale. The acid addition salts of the compounds of formula (I) are obtainable by conversion with the corresponding organic or inorganic acid.

A new class of coupler substances is obtained, with physiologically favorable properties, which exhibit no or only slight mutagenicity. This is extraordinarily surprising, because the 2,4-diaminotoluol, which does not contain the additional alkoxy group, is a known and very powerful mutagen, and so this compound can even be used as a positive standard in the B. N. Ames mutagenicity test (B. N. Ames, J. MacCann and E. Yamasaki, Mut. Res. 31, 347–363 (1975)), in order to test the effectiveness of the test system.

A further advantage of the coupler substances for the formula (I) is the tone of the coloration. Regardless of the radical $R^2$, in coloring with the conventional developer substance 2,5-diaminotoluol, for example, a pure, cold blue is obtained, without any unpleasant red or green components.

The colorings attainable with the new coupler substances furthermore have great depth of color and unexpectedly great light fastness.

The subject of the present invention is also a means for oxidative dyeing of hair based on a developer substance and coupler substance combination, which as the coupler substance includes at least one 5-alkoxy-2,4-diaminoalkylbenzene of the formula (I).

The coupler substances of formula (I) should be used in the hair dye compositions either as free bases, or in the form of their physiologically compatible salts with inorganic or organic acids, for example in the form of chloride, sulfate, phosphate, acetate, propionate, lactate or citrate. The compounds of formula (I) are readily soluble in water. They also have an excellent shelf life, especially as a component of the hair dye compositions described here.

In the hair dye compositions, the coupler substances of formula (I) should be at a concentration of 0.01 to 3.0% by weight, preferably 0.1 to 2.0% by weight.

The coupler substance of formula (I) is generally used in an approximately molar amount with respect to the developer substances used. Although equimolar use also proves to be suitable, it is still not disadvantageous to use somewhat less or more of the coupler substance. Nor is it necessary for the developer component and the coupler component to be single products; instead, the developer component can be a mixture of known developer substances, and the coupler component can be a mixture of the compound according to the invention and known coupler substances. Furthermore, other known coupler substances can also be contained in the hair dye compositions, these coupler substances being, in particular, resorcin, 4-chlororesorcin, 2-methylresorcin, 2-amino-4-(2'-hydroyethyl)-anisole, 2,4-diaminophenylethanol, 2,4-diaminophenoxyethanol, 1,5-dihydroxytetraline, m-aminophenol, 3-amino-2-methylphenol, 3-amino-6-methylphenol, 4-hydroxy-1,2-methylenedioxybenzene, 4-amino-1,2-methylenedioxybenzene, 2,4-diaminoanisole and 2,4-diaminophenetol.

Of the known developer substances, the following are particularly suitable as ingredients of the hair dye compositions according to the invention: 1,4-diaminobenzene, 2,5-diaminotoluol, 2,5-diaminoanisole, 2,5-diaminobenzylalcohol, 3-methyl-4-aminophenol, and 4-aminophenol.

The total quantity of developer subtance and coupler substance combination contained in the hair dye compositions described here should be approximately 0.1 to 5.0% by weight and preferably 0.5 or 3.0% by weight.

To attain certain shades, conventional direct-steeping dyes can also be included, for instance triphenylmethane dyes such as Diamond Fuchsine (C. I. 42 510) and Leather Ruby H. F. (C. I. 42 520); aromatic nitro dyes such as 2-amino-4,6-dinitrophenol, 2-nitro-1,4-diaminobenzene, 2-amino-4-nitrophenol and 2-amino-5-nitrophenol; azo dyes such as Acid Brown 4 (C. I. 14 805); and anthraquinone dyes such as 1,4 diaminoanthraquinone.

The new hair dye compositions can also contain color precursors that couple to themselves, such as 2-amino-5-methylphenol, 2-amino-6-methylphenol, 2-amino-5-ethoxyphenol or 2-propylamino-5-aminopyridine.

It is understood that the coupler and developer substances and other color components, if they are bases, can be used in the form of the physiologically compatible acid addition salts, for example in the form of hydrochloride, sulfate, acetate and lactate or—if they have aromatic OH groups—in the form of salts with bases, for example as alkali phenolates, can be used. Furthermore, still further convention cosmetic additives can be present in the hair dye compositions, such as antioxidation agents like ascorbic acid or sodium sulfite, perfume oils, complex formers, wetting agents, emulsifiers, thickeners, conditioners and others.

The preparation form may for instance be a solution, in particular an aqueous or aqueous-alcohol solution. The particularly preferred preparation forms, however, are a creme, gel or emulsion.

Their composition is a mixture of the dye components with the usual additives for such preparations.

Typical additives in solutions, cremes, emulsions or gels are, for example, solvents such as water; lower, and aliphatic alcohols, such as ethanol, propanol and isopropanol, and multivalent alcohols, such as ethylene glycol, 1,2-propylene glycol and glycerine; and wetting agents or emulsifiers from the classes of anionic, cationic, amphoteric or nonionogenic surface-active substances such as fatty alcohol sulfates, alkyl sulfonates, alkylbenzene sulfonates, alkyltrimethylammonium salts, alkyl betaines, ethoxylated fatty alcohols, ethoxylated nonyl phenols, fatty acid alkanolamides, ethoxylated fatty acid esters, as well as thickeners such as higher fatty alcohols, bentonite, starch, polyacrylic acid, cellulose derivatives, alginates, vaseline, paraffin oil and fatty acids, as well as conditioners such as lanolin derivatives, cholesterol, pantothenic acid and betaine. The aforementioned ingredients are used in the quantities typical for such purposes; for example, the wetting agents and emulsifiers can be contained in the preparations in concentrations of approximately 0.5 to 30% by weight, while the thickeners can be contained in a quantity of approximately 0.1 to 25% by weight.

Depending on the composition, the hair dye compositions according to the invention may react as slightly acidic, neutral or alkaline. In particular, they have a pH value in the alkaline range between 8.0 and 11.5, the adjustment preferably being performed with ammonia. Organic amines, such as monoethanolamine and triethanolamine, or inorganic bases such as sodium hydroxide and potassium hydroxide can also be used, however.

For use as an oxidative hair coloring, the above-described hair dye compositions are mixed immediately prior to use with an oxidation agent, and an amount sufficient for the hair coloring treatment and depending upon the fullness of the hair—typically approximately 60 to 200 g—of this mixture is applied to the hair. As an oxidation agent for developing the hair color, hydrogen peroxide is primarily recommended, for example as a 6% aqueous solution, or its addition compounds of urea, melamine, or sodium borate. The mixture is left on the hair for approximately 10 to 45 minutes, preferably 30 minutes, at 15° to 50° C.; the hair is then rinsed with water and dried. Optionally, this rinsing can be followed by washing with a shampoo, and an optional later rinse can be done with a weak physiologically compatible organic acid, such as citric acid or tartaric acid.

In terms of the coloring options, the hair dye compositions according to the invention, depending on the type and composition of the color components, offer a broad palette of different gradations of color, ranging from blonde to brown, ash, matte, golden to blue tones. The shades are distinguished by good color intensity and adequate light fastness.

EXAMPLES OF PREPARATION

Example 1

2,4-diamino-5-ethoxytoluol dihydrochloride

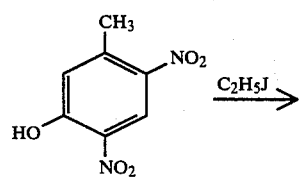

-continued

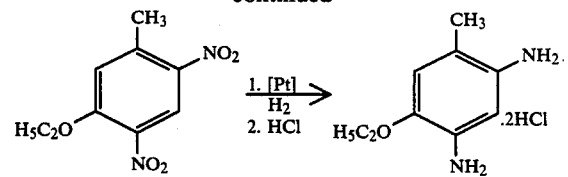

Step 1: 2,4-dinitro-5-ethoxytoluol 2.5 g (12.5 mmol) of 2,4-dinitro-5-methylphenol (I. R. Gibbs and P. W. Robertson, J. Chem. Soc. (London) 105, 1885) are dissolved in 12.5 ml of dioxane, added to 1.5 ml (19 mmol) of 2-iodoethane and 3.5 ml (25 mmol) of triethylamine and heated for 24 hours to 80° C. The reaction mixture is then poured over ice. The yellow crystals that precipitate out are isolated by suction. 2.2 g (77% of theoretical) of the ethoxy compound, having a melting point of 92° to 93° C., are obtained.

NMR spectrum (solvent, CDCl$_3$): 8.67 (s, 3-H), 6.97 (s, 6-H), 4.30 (q, —O—CH$_2$—, J=7 Hz), 2.72 (s, CH$_3$), 1.53 (t, O—CH$_2$CH$_3$, J=7 Hz).

For this and all the following NMR spectra, the following specifications apply:

Apparatus: Varian XL100, 100 MHz spectrum;
s=singlet; d=doublet; t=triplet; q=quartet; m=muliplet
Internal standard: tetramethylsilane with delta$_{TNS}$=0 ppm Step 2: 2,4-diamino-5-ethoxytoluol dihydrochloride The nitro compound of step 1 is dissolved in ethanol and catalytically hydrogenated with hydrogen in platinum. After the absorption of the theoretical quantity of hydrogen, the catalyst is filtered out, and after concentration, the solution is mixed with concentrated aqueous hydrochloric acid solution. The resultant dihydrochloride of the 2,4-diamino-5-ethoxytoluol is removed by suction and dried. It decomposes at 210° C.

Example 2

2,4-diamino-5-(2'-hydroxyethyl)oxytoluol dihydrochloride

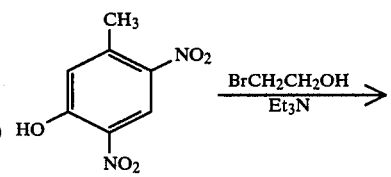

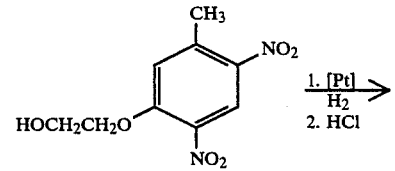

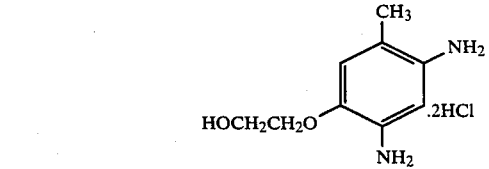

Step 1: 2,4-diamino-5-(2'-hydroxyethyl)oxytoluol 1.0 g (5 mmol) of 2,4-dinitro-5-methylphenol (see example 1) are dissolved in 5 ml of dioxane, mixed with 0.5 ml (7 mmol) of 2-bromoethanol and 1.7 ml (12 mmol) of triethylamine and heated for 36 hours to 85° C. Next the reaction mixture is poured over ice. The yellow crystals are isolated by suction. 0.6 g (49% of theoretical) of the dinitrophenol ether having a melting point of 100° C. is obtained.

NMR spectrum (solvent, $CDCl_3$): 8.72 (s, 3-H), 7.02 (s, 6-H), 4.34 (t, —$CH_2$—, J=4.5 Hz), 4.05 (t, —$CH_2$—, J=4.5 Hz), 2.73 (s, $CH_3$), 2.5–1.7 (wide, OH; when the sample is shaken with $D_2O$ the signal disappears).

Mass spectrum: 242 (M+, 22%), 198 (10%), 182 (25%), 181 (84%), 165 (10%), 135 (16%), 109 (16%), 107 (17%), 73 (37%), 46 (100%).

Given in m/e (relative intensity).

Step 2: 2,4-diamino-5-(2'-hydroxyethyl)oxytoluol

The catalytic reduction of the nitro compound, done analogously to example 1, produces the diamino compound as dihydrochloride, which decomposes without melting from 45° C. onward.

NMR spectrum (solvent, DMSO-$d_6$): 7.62 (s, 3-H), 7.18 (s, 6-H), 8.6–6.0 (very wide, +$NH_3$; the signal disappears if the sample is shaken with $D_2O$), 4.13 (t, —$CH_2$—, J=4.5 Hz), 3.78 (t, —$CH_2$—, J=4.5 Hz), 2.40 (s, $CH_3$).

EXAMPLES FOR HAIR DYE COMPOSITIONS

Example 3 hair dye composition of gel form

| 0.10 g | 2,4-diamino-5-(2'-hydroxyethyl)oxytoluol dihydrochloride |
| --- | --- |
| 0.5 g | m-aminophenol |
| 0.90 g | p-toluylenediamine sulfate |
| 0.40 g | resorcin |
| 0.30 g | ascorbic acid |
| 1.00 g | hydroxyethyl cellulose, highly viscous |
| 5.00 g | lauryl alcohol diglycolether sulfate, sodium salt (25% aqueous solution) |
| 10.00 g | ammonia (22% aqueous solution) |
| 82.25 g | water |
| 100.00 g | |

50 g of the above hair dye composition is mixed, shortly prior to use, with 50 ml of hydrogen peroxide solution (6%) and the mixture is then applied to white human hair. After acting for 30 minutes at 40° C., the hair is rinsed with water and dried. The hair is dyed ash blonde.

Example 4 hair dye composition in the form of an aqueous solution

| 0.15 g | 2,4-diamino-5-ethoxytoluol dihydrochloride |
| --- | --- |
| 0.80 g | 4-amino-2-hydroxymethylphenol |
| 0.20 g | 5-amino-2-methylphenol |
| 0.95 g | p-toluylenediamine sulfate |
| 0.05 g | 2-nitro-p-phenylenediamine |
| 0.02 g | 4-(2'-ureidoethyl)aminonitrobenzene |
| 0.15 g | sodium sulfite |
| 10.00 g | ethanol (95%) |
| 10.00 g | ammonia (25%) |
| 5.00 g | lauryl alcohol diglycolether sulfate, sodium salt (28% aqueous solution) |
| 72.68 g | water |
| 100.00 g | |

25 g of the above hair dye composition is mixed shortly before use with 25 ml of hydrogen peroxide solution (6%) and the mixture is then applied to white human hair. After it acts for 45 minutes at 35° C., the hair is rinsed with water and a dilute citric acid and dried. The hair is dyed a natural brown tone.

Example 5 hair dye solution

| 1.00 g | 2,4-diamino-5-(2'-hydroxyethyl)oxytoluol dihydrochloride |
| --- | --- |
| 3.00 g | 2-ethyl-1,4-diaminobenzene dihydrochloride |
| 0.60 g | N—(2'-hydroxyethyl)-3,4-methylenedioxyaniline |
| 0.50 g | 3-amino-5-hydroxy-2,6-dimethoxypyridine hydrochloride |
| 0.10 g | m-aminophenol |
| 10.00 g | ammonia (25% aqueous solution) |
| 84.80 g | water |
| 100.00 g | |

Shortly prior to use, 10 g of the above hair dye composition is mixed with 10 ml of hydrogen peroxide solution (6%) and the mixture is allowed to act for 30 minutes at 40° C. on blonde natural hair. The hair is then rinsed with water and dried. The hair is dyed black. All percentages recited in the above patent application, unless otherwise defined, represent percents by weight.

We claim:

1. A compound of the formula (I)

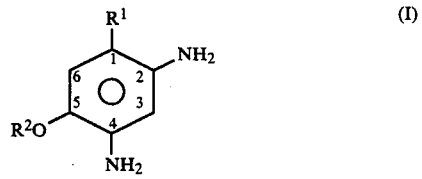

where $R^1$ is methyl or ethyl and $R^2$ is an alkyl radical having 2 to 4 carbon atoms, a monohydroxyalkyl radical having 2 to 4 carbon atoms or a dihydroxyalkyl radical having 3 to 4 carbon atoms, or a physiologically acceptable acid addition salt thereof.

2. 2,4-diamino-5-(2'-hydroxyethyl)oxytoluol or a physiologically acceptable acid addition salt thereof as defined in claim 1.

3. 2,4-diamino-5-ethoxytoluol or a physiologically acceptable acid addition salt thereof as defined in claim 1.

4. A composition for oxidative dyeing of hair comprising a developer compound and a coupler compound of the formula (I)

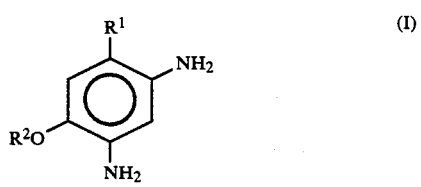

where $R^1$ is methyl or ethyl and $R^2$ is an alkyl radical having 2 to 4 carbon atoms, a monohydroxyalkyl radical having from 2 to 4 carbon atoms or a dihydroxyalkyl radical having from 3 to 4 carbon atoms, or a physiologically acceptable acid addition salt thereof, wherein the coupler compound is capable of reacting with the developer compound under oxidative conditions and is present in an amount effective to react with the developer compound under oxidative conditions, together with a physiologically acceptable inert carrier.

5. A composition as defined by claim 4, characterized in that $R^1$ is methyl.

6. A composition as defined by claim 4 characterized in that the compound of the Formula (I) is selected from the group consisting of 2,4-diamino-5-(2'-hydroxyethyl)oxytoluol and 2,4-diamino-5-ethoxytoluol or a physiologically acceptable acid addition salt thereof.

7. A composition as defined by claim 4 characterized in that the coupler substance of formula (I) is contained in a quantity of from 0.01 to 3.0% by weight.

8. A composition as defined by claim 4, characterized in that the developer substance is selected from the group consisting of 1,4-diaminobenzene, 2,5-diaminotoluol, 2,5-diaminoanisole, 2,5-diaminobenzylalcohol, 2,5-diaminophenylethanol, 2-methyl-4-aminophenol, 3-methyl-4-aminophenol, 2-aminomethyl-4-aminophenol and 4-aminophenol.

9. A composition as defined by claim 4, characterized in that it additionally contains a known coupler substance, which is selected from the group consisting of resorcin, 4-chlororesorcin, 2-methylresorcin, 2-amino-4-(2'-hydroxyethyl)aminoanisole, 2,4-diaminophenylethanol, 2,4-diaminophenoxyethanol, 2,4-diaminoanisole, 2,4-diaminophenetole, 1,5-dihydroxytetraline, m-aminophenol, 3-amino-2-methylphenol, 3-amino-6-methylphenol, 4-hydroxy-1,2-methylenedioxybenzene, 4-amino-1,2-methylenedioxybenzene, 4-(2'-hydroxyethyl)-amino-1,2-methylenedioxybenzene, 3,5-diamino-2,6-dimethoxypyridine, 3,5-diamino-2,6-bis-(2'-hydroxyethyl)oxypyridine.

10. A composition as defined by claim 5, characterized in that the compound of formula (I) is selected from the group consisting of 2,4-diamino-5-(2'-hydroxyethyl)oxytoluol and 2,4-diamino-5-ethoxytoluol or a physiologically acceptable acid addition salt thereof.

* * * * *